(12) United States Patent
Rafter

(10) Patent No.: US 7,578,791 B2
(45) Date of Patent: Aug. 25, 2009

(54) AUTOMATED MYOCARDIAL CONTRAST ECHOCARDIOGRAPHY

(75) Inventor: Patrick Rafter, Windham, NH (US)

(73) Assignee: Koninklijke Philips Electronics NV, Eindhoven (NL)

( * ) Notice: Subject to any disclaimer, the term of this patent is extended or adjusted under 35 U.S.C. 154(b) by 0 days.

(21) Appl. No.: 10/599,769

(22) PCT Filed: Apr. 16, 2005

(86) PCT No.: PCT/IB2005/051111

§ 371 (c)(1),
(2), (4) Date: Oct. 9, 2006

(87) PCT Pub. No.: WO2005/099579

PCT Pub. Date: Oct. 27, 2005

(65) Prior Publication Data

US 2007/0276239 A1    Nov. 29, 2007

Related U.S. Application Data

(60) Provisional application No. 60/562,846, filed on Apr. 16, 2004.

(51) Int. Cl.
A61B 8/00    (2006.01)
A61B 8/14    (2006.01)

(52) U.S. Cl. .................................... 600/447; 600/458
(58) Field of Classification Search ................ 600/437, 600/442–458
See application file for complete search history.

(56) References Cited

U.S. PATENT DOCUMENTS

| | | | |
|---|---|---|---|
| 5,947,904 | A | 9/1999 | Hossack et al. |
| 6,503,203 | B1 | 1/2003 | Rafter et al. |
| 2001/0056236 | A1 | 12/2001 | Angelsen |
| 2003/0195421 | A1 | 10/2003 | Demers |
| 2003/0208124 | A1 | 11/2003 | Poland |

*Primary Examiner*—Eric F Winakur
*Assistant Examiner*—Michael T Rozanski
(74) *Attorney, Agent, or Firm*—W. Brinton Yorks, Jr.

(57) ABSTRACT

A myocardial contrast echo exam is performed by the use of a two dimensional array transducer probe. The probe is held against a selected acoustic window of the body and first and second image planes through the heart are imaged and the plane orientations stored. Settings to optimize the images may also be stored for the two plane orientations. A contrast agent is infused and the resting heart scanned through the acoustic window. Upon actuation of a user control the ultrasound system automatically acquires images of the selected image planes through the acoustic window. Stress is applied to the heart to increase the heart rate and automatic acquisition sequence is repeated to acquire the images with the heart under stress. The at-rest and stress images may be compared to analyze the reperfusion of the myocardium of the heart.

20 Claims, 4 Drawing Sheets

AUTOMATED MYOCARDIAL CONTRAST ECHOCARDIOGRAPHY

CROSS REFERENCE TO RELATED APPLICATION

This application claims the benefit of U.S. provisional application Ser. No. 60/562,846 filed Apr. 16, 2004, which is incorporated herein.

This invention relates to medical diagnostic ultrasound systems and, in particular, to the use of ultrasonic imaging to assess the state of the myocardium.

Stress echocardiography (stress echo) examinations have been in widespread use for a number of years to assess the functioning of the heart. In a stress echo exam a patient is first examined while resting. The heart is imaged with ultrasound (echocardiography) from a number of perspectives which acquire different cross-sectional views of the heart in real time. One common imaging perspective is the apical four-chamber (AP4) view in which the heart is viewed from the apex in a cross-section which shows both atria and both ventricles. Another common imaging perspective is the apical three-chamber (AP3) view in which the cross-sectional image from the apex shows the left atrium and the left ventricle, the aorta, and the mitral and aortic valves. A third common imaging perspective is the apical two-chamber view (AP2) in which the left ventricle and left atrium and the mitral valve are seen in the cross-sectional image from the apex. Real time images of the beating heart from one and usually several of these viewing perspectives are acquired and saved while the patient is at rest. The heart is then stressed either by physical exercise or by application of a pharmacological stress agent such as dobutamine. Real time image sequences are acquired from the same viewing perspectives while the heart is under stress. The stressed and unstressed images are then replayed side-by-side so that the physician can assess the performance of the heart under both conditions and make appropriate diagnoses.

A somewhat similar protocol for diagnosing the condition of the heart muscle, called a myocardial contrast echocardiography (MCE) examination is presently undergoing clinical investigation. The MCE exam is based upon the principle of myocardial reperfusion analysis exemplified by FIGS. 1 and 2 which are drawn from U.S. Pat. No. 5,833,613 (Averkiou et al.) FIG. 1 illustrates a heart cycle waveform 230, indicating the pulsatile action of bloodflow. During the heart cycle new blood is pumped into the coronary arteries and infuses the capillary structure of the myocardium. Advantage is taken of this reinfusing action by repetitively measuring the degree of contrast agent reinfusion at a constant point in the heart cycle, but following continually differing phases of microbubble destruction. In FIG. 1 the X points of reinfusion measurement all occur at the same phase of the heart cycle. The X points are preceded by differing times at which the microbubbles are destroyed, as indicated by arrows 232, 234, and 236, which successively precess to earlier times in the heart cycle. This means that each Xn point of FIG. 12 will be a later Xn point on the perfusion curve 224 of FIG. 13. Since the purpose of ultrasonic transmission at the times of arrows 232, 234, and 236 is to destroy the microbubbles, it is not necessary to receive and analyze the returning echoes at these times. Echo reception and analysis is done at the times of the Xs, and the Xs shown in FIG. 12 can be plotted as the successive Xs in FIG. 13 due to the precession of the destruction time phases indicated by the arrows.

The reperfusion curve may be created from these measurements as indicated in FIG. 2. Ultrasonic pulses are transmitted at time td (corresponding to times 232, 234, and 236 in FIG. 1) to destroy the microbubbles in the myocardial capillary bed as indicated by level 30 of the curve. A short time later pulses are transmitted again, the echoes received and imaged to this time measure the degree of microbubble reinfusion, either by destroying reinfused microbubbles and recording the destruction events, or by counting or integrating pixels in the area which show reinfused microbubbles. The measure of the number of microbubbles reinfused to the region is plotted as a point X of the curve 224. Pulses can be repetitively transmitted and echoes received to plot a sequences of X points on the curve as shown in FIG. 2. A healthy patient may experience full reperfusion, at which the level of curve 224 reaches the steady-state perfusion level 220, in only a few heart cycles, whereas a patient with obstructed coronary arteries may require many heart cycles (the time between one of the arrows and one of the Xs in FIG. 1) before the myocardium is fully reperfused with new blood and contrast agent.

This principle is used in the MCE exam to assess the rate of reperfusion and hence the degree of obstruction of blood flow to the myocardium. In making this assessment it is desirable to be able to view the myocardium from a number of different imaging perspectives as described above. With conventional imaging systems this can be a tedious and time consuming process as a new acoustic window must be located for each view and the imaging parameters adjusted for the best image from each window. It must be remembered that the patient is undergoing contrast infusion during this time, using greater amounts of contrast agent as the exam is prolonged. Accordingly it would be desirable to be able to speed up an MCE exam to spare the patient from extended infusion periods and to conserve the time of the physician and the use of contrast agent.

In accordance with the principles of the present invention, an ultrasonic contrast imaging procedure which requires a number of imaging perspectives such as an MCE exam is facilitated by the use of a two dimensional array probe from which one or more viewing perspectives can be adjusted by manual adjustment of the beam steering. After a first imaging perspective is obtained through a favorable acoustic window of the body the same acoustic window is used for a subsequent imaging perspective by adjusting the position of another image plane by electronic beam steering. The different viewing perspectives and optimized imaging parameters are set in this way at the outset of the procedure. During the exam the imaging system can automatically step through the sequence of preset views and imaging parameters, all without the need to reposition the probe on the body of the patient. Desired imaging perspectives pre- and post-stress can thus be obtained rapidly and reliably.

Figure 1:
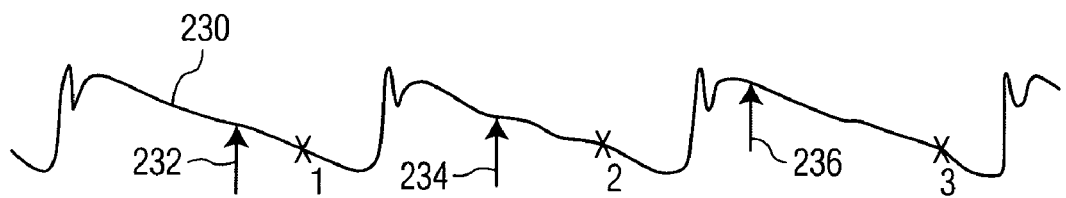
FIG. 1 illustrates the acquisition of perfusion measurements after different periods of a heart cycle waveform.
Figure 2:
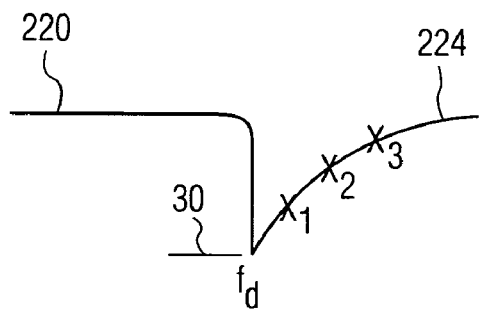
FIG. 2 illustrates the creation of a perfusion curve from the measurements taken in accordance with FIG. 1.

An MCE exam may be performed with a conventional ultrasound system in the following manner. Before starting the infusion of contrast agent into the body of the patient, the sonographer will begin scanning the patient's heart to locate the best acoustic windows on the patient's body for the desired viewing perspectives needed for the exam. For example, if AP4, AP2 and AP3 views are all needed, the sonographer will move the ultrasound probe to different acoustic windows through and below the patient's ribs, looking for the best acoustic window for each view. Once the sonographer has found the acoustic windows the contrast agent is administered to the patient.

With the patient at rest the sonographer will place the probe at the AP4 acoustic window and begin to acquire AP4 images at a low Mechanical Index (MI, or acoustic power). The sonographer adjusts the machine settings to obtain the best image. The settings involved may include settings such as TGC, gain, dynamic range, lateral gain, the greyscale or color map used, etc. The sonographer will set the sequence of triggering intervals for image acquisition. The patient's ECG is monitored and the ECG waveform is used by the ultrasound system to trigger the acquisition of images in synchronization with and at the proper phases of the heart cycle. The triggering intervals are the number of heart cycles between a high MI transmission for microbubble destruction in the myocardium and the subsequent acquisition of an image as the myocardium is reperfused with new contrast agent. A typical sequence may be [1, 1, 1, 2, 2, 2, 4, 4, 4, 8, 8, 8]. In this sequence three images are first acquired with only one heart cycle between microbubble destruction and image acquisition. This is followed by three images with a two heart cycle interval between destruction and acquisition; three images with a four heart cycle interval between destruction and acquisition; and three images with an eight heart cycle interval between destruction and acquisition. AP4 contrast images are then acquired using the image settings and the high MI/low MI triggering interval sequence set by the sonographer. The AP4 images are saved for later use.

In some ultrasound systems it is possible to save the image settings and the triggering interval sequence. If so, the image settings and the triggering interval sequence are stored for the AP4 view. The sonographer then moves the probe to the AP2 acoustic window and observes AP2 images at a low MI. The sonographer adjusts the machine settings for the optimal AP2 image and sets the triggering interval sequence for AP2 acquisition or recalls the triggering interval sequence previously stored if applicable. AP2 contrast images are then acquired using the image settings and the high MI/low MI triggering interval sequence set by the sonographer. The AP2 images are saved for later use. The image settings and triggering interval sequence for the AP2 images are saved if this capability is present on the machine.

The probe is then moved to the AP3 acoustic window and the image settings adjusted for the best image. A previous triggering interval sequence is recalled or a new sequence for AP3 images is set by the sonographer. AP3 contrast images are then acquired using the image settings and the high MI/low MI triggering interval sequence set by the sonographer. The AP3 images are saved for later use. The image settings and triggering interval sequence for the AP3 images are saved if this capability is present on the machine.

The acquisition of at-rest images is now complete and the patient begins physical exercise or a stress agent such as dobutamine (or a vasodilator such as adenosine or dipyridamole) is administered to the patient. When the patient has attained the desired high heart rate or other desired physiologic sign, the previous sequence of AP4, AP2, and AP3 images are acquired, this time with the heart under stress. The stored image settings and triggering interval sequence are used if possible. At the end of stress image acquisition the acquired images are stored. The patient is cared for until normal heart rhythm is restored. Diagnosis using the saved images then takes place by comparing at-rest and stress images side-by-side using the different views and appropriate triggering interval image comparisons. If an abnormality is detected, a more thorough diagnosis may occur.

The image acquisitions described above can take twenty minutes or more. This is due to the need to reposition the probe to a new acoustic window and find the desired image plane for each new viewing perspective, as well as the need to repeatedly adjust image settings and triggering interval sequences when these parameters cannot be saved and reused. It would be desirable to reduce this exam time if possible.

Figure 3:
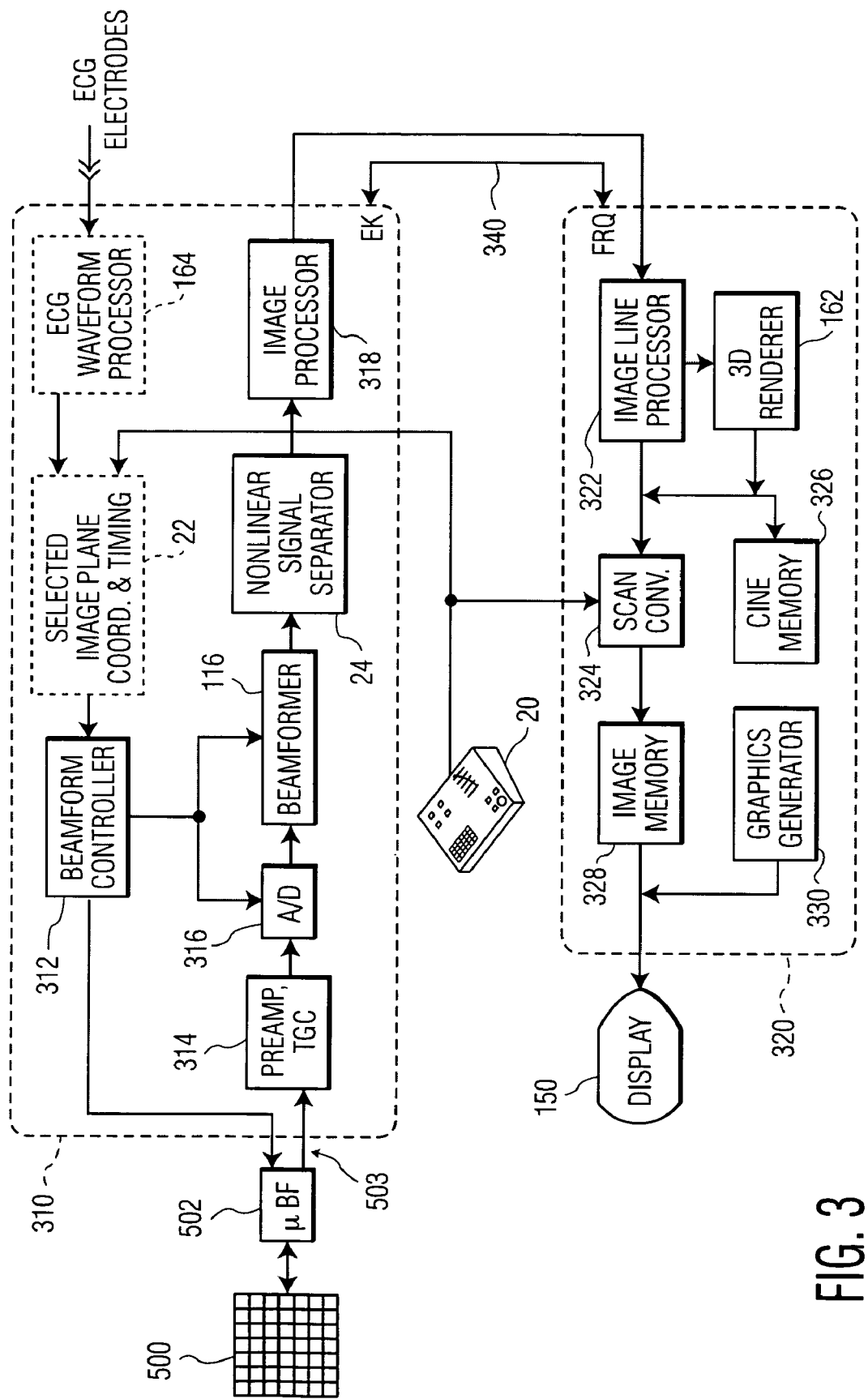
FIG. 3 illustrates in block diagram form an ultrasonic diagnostic imaging system constructed in accordance with the principles of the present invention.

Referring now to FIG. 3, an ultrasonic diagnostic imaging system constructed in accordance with the principles of the present invention is shown in block diagram form. An ultrasound probe includes a two dimensional array transducer 500 and a micro-beamformer 502. The micro-beamformer contains circuitry which controls the signals applied to groups of elements ("patches") of the array transducer 500 and does some processing of the echo signals received by the elements of each group. Micro-beamforming in the probe advantageously reduces the number of conductors in the cable 503 between the probe and the ultrasound system mainframe and is described in U.S. Pat. No. 5,997,479 (Savord et al.) and in U.S. Pat. No. 6,436,048 (Pesque).

The probe is coupled to the scanner 310 of the ultrasound system. The scanner includes a beamform controller 312 which is responsive to a user control as described below and provides control signals to the microbeamformer 502, instructing the probe as to the timing, frequency, direction and focusing of transmit beams. The beamform controller also controls the beamforming of received echo signals by its coupling to the analog-to-digital (A/D) converters 316 and the scanner beamformer 116. Echo signals received by the probe are amplified by preamplifier and TGC (time gain control) circuitry 314 in the scanner, then digitized by the A/D converters 316. The digitized echo signals are then formed into beams by the beamformer 116. The echo signals are then processed by a nonlinear signal separator 24 which segments out the nonlinear (e.g., harmonic) components of a microbubble echo signal. A suitable nonlinear signal separator and segmentation processor is described in U.S. patent [application Ser. No. 60/542,259] (Bruce et al.) entitled "ULTRASONIC IMAGING OF PERFUSION AND BLOOD FLOW WITH HARMONIC CONTRAST AGENTS." The signals separated for imaging are then applied to an image processor 318 which performs digital filtering, B mode detection, and Doppler processing, and can also perform other signal processing such as speckle reduction through frequency compounding and other desired image processing techniques.

The echo signals produced by the scanner 310 are coupled to the digital display subsystem 320, which processes the echo signals for display in the desired image format. The echo signals are processed by an image line processor 322, which is capable of sampling the echo signals, splicing segments of beams into complete line signals, and averaging line signals for signal-to-noise improvement or flow persistence. The image lines are scan converted into the desired image format by a scan converter 324 which performs R-θ conversion as is known in the art. The image is then stored in an image memory 328 from which it can be displayed on a display 150. The image in memory is also overlayed with graphics to be displayed with the image, which are generated by a graphics generator 330 which is responsive to a user control. Individual images or image sequences can be stored in a cine memory 326 during capture of individual images or image loops.

For real-time volumetric imaging the display subsystem 320 also includes the 3D image rendering processor 162 which receives image lines from the image line processor 322 for the rendering of a real-time three dimensional image which is displayed on the display 150.

In accordance with the principles of the present invention, multiple planar images of different image planes of the heart are acquired by the probe in rapid succession from the same acoustic window during performance of an MCE exam. Since the 2D array 500 has the ability to steer transmitted and received beams in a wide range of directions and inclinations in front of the array, beams can be steered to scan a variety of different image planes. The planes of the images can have a variety of different orientations with respect to the array and to each other, even when the probe is held stationary against a single acoustic window below or through the ribs. In a preferred embodiment the images exhibit a sector format with the beams of each image emanating from the center of the array. Thus, with the center of the array centered on the acoustic window, images of different viewing perspectives of the heart such as AP2, AP3, and AP4 cross-sectional views can often be obtained from the same acoustic window without moving the probe.

Figure 4:
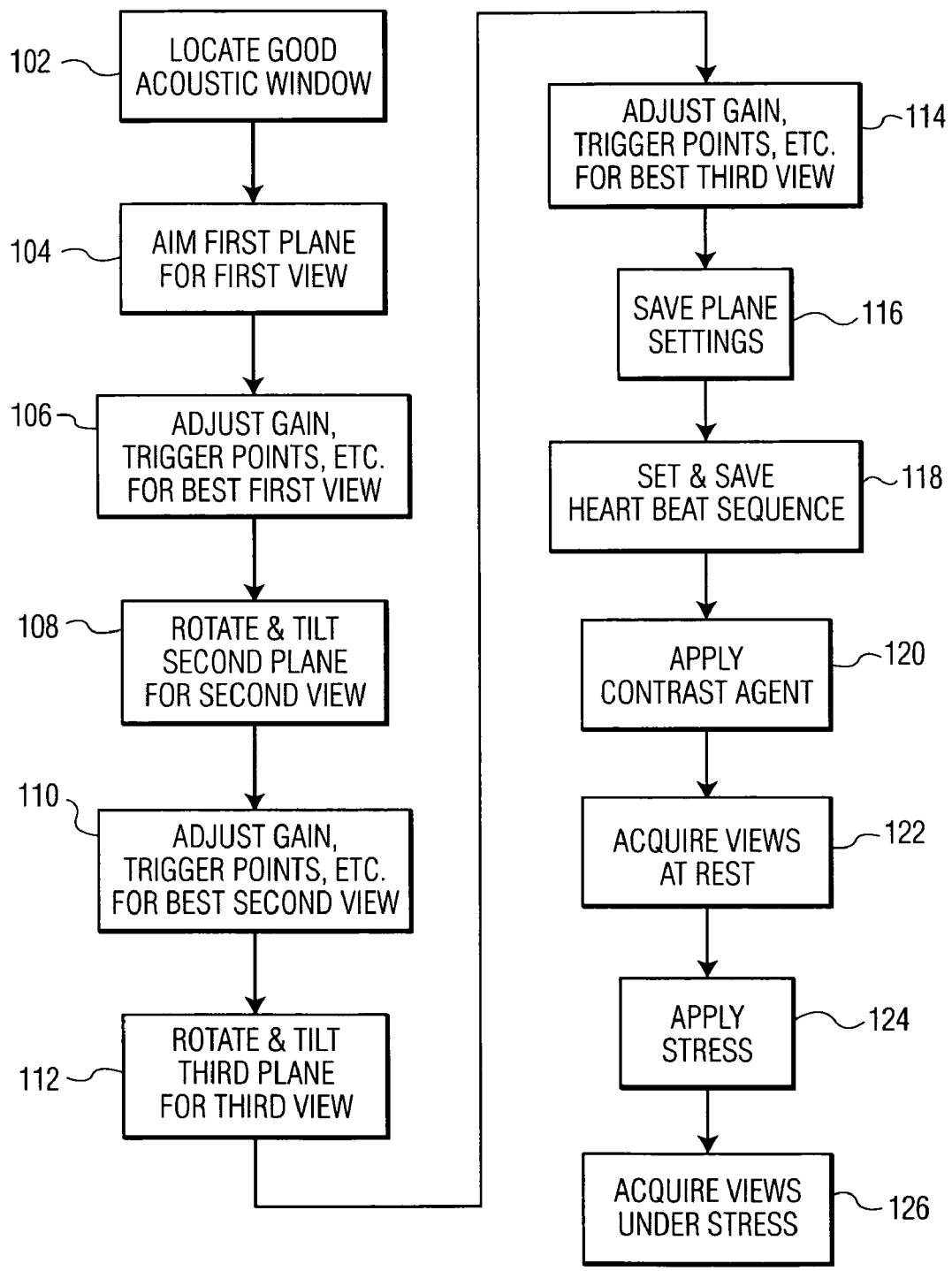
FIG. 4 is a flowchart of the steps in an MCE exam in accordance with the principles of the present invention.

The probe and ultrasound system of FIG. 3 can be used in an MCE examination in accordance with the procedure outlined in the flowchart of FIG. 4. Initially the probe will be scanning a single image plane such as a plane extending normal to the face of the probe and the plane of the array 500. The sonographer maneuvers the probe to locate a good acoustic window (102) to the heart. Typically this might be an acoustic window that would be used to acquire an AP4 view with a conventional probe. The probe is maneuvered until the image plane is positioned to acquire a first viewing perspectives for the exam (104). This might be a desired AP4 cross-sectional view, for instance. The probe is held stationary and the imaging settings and triggering interval sequence are set for this first view (106) and saved. These settings for the first view are saved in a selected image plane coordination and timing store 22 from which they can be recalled automatically and used as imaging control parameters for the beamform controller 312. With the probe still held against the same acoustic window of the body, a control on the ultrasound system control panel 20 such as a trackball, joystick, or knob is manipulated by the sonographer to rotate or tilt the image plane into a second plane orientation suitable for a second viewing perspective of the exam (108). The second viewing perspective may be an AP2 cross-sectional view, for instance. The imaging settings and triggering interval sequence are set for this second view (110) and saved in the selected image plane coordination and timing store 22. With the probe still held against the acoustic window the control panel control is manipulated again to reposition the image plane in a third viewing perspective for the exam (112) such as an AP3 view. The imaging settings and triggering interval sequence are set for this third view (114) and saved in the selected image plane coordination and timing store 22. Alternatively, if the imaging settings for the viewing perspectives have not been saved previously, they are saved at the end of the view selection steps (116). Similarly, if the triggering interval sequence(s) have not bee previously set and saved, this is done at this time (118). The ultrasound system has now been programmed to automatically acquire the sequence of images of different views which are required for the MCE exam.

The infusion of contrast agent to the patient is now started (120) and the probe is repositioned on the chosen acoustic window. The probe may be manipulated until the first viewing perspective is reacquired on the display screen. ECG electrodes which have been placed on the patient are coupled to an ECG waveform processor 164 of the ultrasound system, which provides an ECG waveform to the beamform controller 312. The beamform controller will thereby trigger image acquisition at the desired phases and intervals of the patient's heart cycle. With the first plane view showing on the display screen the sonographer starts the automatic scan sequence by pressing the "Acquire Image Sequence" control on the control panel 20 or, preferably, by depressing a foot switch to start the automatic acquisition of images (122). The preprogrammed sequence of images of different viewing perspectives with preset imaging settings and at the desired heart cycle intervals is then acquired automatically by the ultrasound system by use of the image plane coordinate and timing parameters stored in the store 22 and accessed by the beamform controller 312.

After the at-rest images have been acquired and saved the patient's heart is put under stress to increase the heart rate (124). The probe is placed against the acoustic window again and maneuvered until the first viewing perspective image is reacquired on the screen. The "Acquire" or foot switch control is actuated again to automatically acquire a second sequence of properly oriented and timed images, this time with the heart under stress. At the end of this acquisition the examination of the patient is complete and the images are saved for subsequent analysis and diagnosis. The automation of the acquisition process in accordance with the present invention can enable the entire MCE exam to be completed in approximately one-third of the time required by a conventional ultrasound system.

Figure 5:
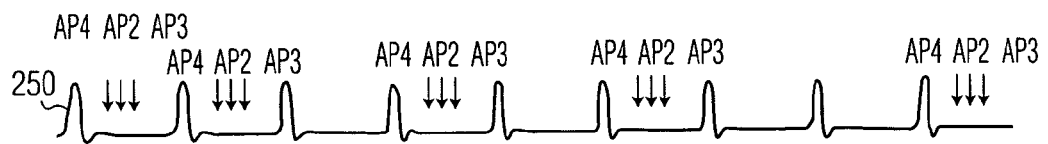
FIGS. 5-7 illustrate different sequences of interleaving the acquisition of different viewing perspectives in accordance with the principles of the present invention.

Since the image planes are repositioned automatically by the ultrasound system, it is possible to acquire more than one view perspective during a single heartbeat and to do this in successive heartbeats if desired. That is, the acquisition of the different view perspective planes can be time-interleaved. Not only can individual planes be interleaved, but scanlines from different view perspectives can be acquired in a time-interleaved manner. In the embodiment of FIG. 5 an ECG waveform 250 is shown which provides the trigger timing reference for acquisition of AP4, AP2, and AP3 images. The arrows above the waveform 250 mark the times at which the images are acquired. It is seen that in this embodiment AP4, AP2, and AP3 images are acquired in rapid succession during a first heart cycle, and again during the next successive heart cycle. The differences between the respective AP4, AP2, and AP3 images show the amount of blood flow and contrast agent which has reperfused the myocardium in the different views in a single heart cycle. It is then seen that a heart cycle is skipped before another set of AP4, AP2, and AP3 images are acquired. A comparison of the images on either side of the skipped heart cycle will reveal the degree of reperfusion of the myocardium over the span of two heart cycles. This sequencing is repeated by skipping another heart cycle before reacquiring the three views, then two heart cycles are skipped before another acquisition of the AP4, AP2, and AP3 views is performed, which reveals the degree of reperfusion of the myocardium over the span of three heart cycles. Corresponding pixels on corresponding images can be used to produce reperfusion curves 224 for selected points of the myocardium.

Several implementations of the sequence of FIG. 5 are possible. One is that each image is a high MI image. During the first heart cycle the three transmissions will destroy the microbubbles in the three view slices. The three high MI transmissions during the next heart cycle will measure the amount of contrast which has reinfused each view slice over the duration of one heart cycle. These high MI transmissions will destroy the microbubbles in the three view slices again so that the three high MI transmissions during the fourth heart cycle will measure the amount of contrast which has reinfused each view slice over the intervening two heart cycle time interval. The destruction of these transmissions will enable the same measurement to be made during the sixth heart cycle, which in turn will cause microbubble destruction which enables the reperfusion of contrast over an interval of three heart cycles to be measured by the transmissions occurring during the ninth heart cycle.

Another implementation is to transmit a mixture of high MI and low MI signals. For instance, high MI transmissions can be performed during the first heart cycle and low MI transmissions (relatively nondestructive) during the remaining heart cycles. This would cause the reperfusion occurring in one heart cycle to be sampled during the second heart cycle; the reperfusion occurring after three heart cycles to be sampled during the fourth heart cycle; the reperfusion occurring after five heart cycles to be sampled during the sixth heart cycle; and so forth.

Figure 6:
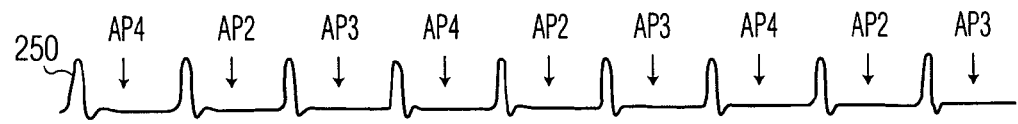
Figure 7:
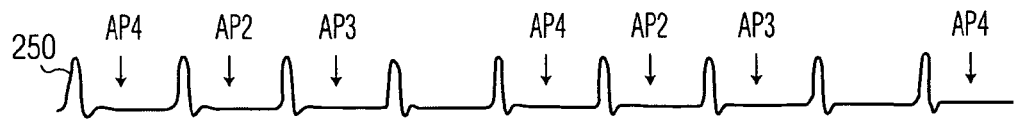

The embodiment of FIG. 6 shows the acquisition of a single view perspective during each successive heart cycle, with a different view perspective acquired from one heart cycle to the next. This means that there is a three heart cycle interval between successive AP4 views, between successive AP3 views, and between successive AP2 views. This time interleaving with each heart cycle enables the acquisition of images of the same view with lengthy intervening replenishment intervals but with efficient use of each heart cycle for rapid acquisition of the desired images. The embodiment of FIG. 7 is a modification of the triggering sequence of FIG. 6 with a heart cycle skipped after each group of different images. Thus, there is a four heart cycle interval between successive images of the same type in the sequence of FIG. 7. In the embodiments of FIGS. 6 and 7 each transmission is a high MI transmission.

The above embodiments and sequences which refer to planar images are also applicable to volumetric acquisition where subvolumes with finite thickness are acquired rather than planar slices with negligible thicknesses. Thus, the term "plane" as used herein also encompasses the term subvolume.

What is claimed is:

1. An ultrasonic diagnostic imaging system which acquires images of differently oriented image planes of a patient in rapid succession comprising:
   a probe including a two dimensional array transducer;
   a beamformer, coupled to the array transducer, for scanning beams over a variety of different directions and inclinations with respect to the array transducer;
   a beamformer controller programmable to scan beams over differently oriented image planes in a sequence of image planes until acquisition of the image planes has been completed;
   an image processor coupled to the beamformer;
   a display coupled to the image processor;
   a plane orientation control, coupled to the beamformer controller, for adjustment of the orientations of a plurality of image planes relative to selected anatomy;
   a storage device responsive to the plane orientation control and operative to store parameters of different image plane orientations selected by operation of the plane orientation control; and
   an acquisition control, coupled to the beamformer and responsive to the stored parameters, for initiation in a diagnostic exam of the acquisition of a sequence of image planes in the selected succession of different orientations with respect to the selected anatomy.

2. The ultrasonic diagnostic imaging system of claim 1, further comprising a source of patient heart waveforms coupled to the beamformer controller.

3. The ultrasonic diagnostic imaging system of claim 1, wherein the image processor further comprises a contrast agent image processor.

4. The ultrasonic diagnostic imaging system of claim 1, wherein the plane orientation control further comprises a manually operated user control; and wherein the storage device further comprises:
   a storage device for storing scanning parameters for a plurality of plane orientations selected by the user control.

5. The ultrasonic diagnostic imaging system of claim 4, further comprising a plurality of imaging parameters which may be adjusted by a user; and
   wherein the storage device further comprises a storage device for storing adjusted imaging parameters.

6. The ultrasonic diagnostic imaging system of claim 5, wherein the beamformer controller is responsive to stored scanning parameters and imaging parameters upon activation of the acquisition control.

7. A method for operating the ultrasonic diagnostic imaging system of claim 1 to perform the acquisition of ultrasonic images of a plurality of differently oriented image planes in rapid succession comprising:
   aiming a first image plane of a two dimensional array probe through an acoustic window of a body;
   reaiming the image plane through the acoustic window by use of the plane orientation control to image a second image plane of a different orientation than the first image plane;
   storing information defining the orientation of the second image plane in the storage device; and
   initiating a sequence of image acquisition which acquires an image of the first image plane followed by an image of the second image plane by use of the stored information.

8. The method of claim 7, wherein reaiming further comprises reaiming the image plane through the same acoustic window as that of the first image plane.

9. The method of claim 8, further comprising storing information defining the orientation of the first image plane in the storage device,
   wherein initiating further comprises using the stored information of the first image plane.

10. The method of claim 7, further comprising infusing the body with an ultrasonic contrast agent.

11. The method of claim 10, further comprising, following infusing, applying stress to the body and,
   following applying, repeating the initiating step.

12. The method of claim 10, wherein the body comprises the heart and wherein the myocardium of the heart is infused with the contrast agent.

13. The method of claim 12, wherein, in the aiming and reaiming steps, the first image plane comprises one of an AP4, AP2, or AP3 view of the heart, and the second image plane comprises a different one of an AP4, AP2, or AP3 view of the heart.

14. The method of claim 7, further comprising adjusting an image parameter after at least one of the aiming and reaiming steps; and storing the adjusted image parameter for each step,
wherein initiating further comprises using the stored adjusted image parameter during image acquisition.

15. A method for operating the ultrasonic diagnostic imaging system of claim 1 to acquire diagnostic ultrasound images of the heart comprising:
maintaining the two-dimensional array transducer in contact with an acoustic window of a body to image a first plane of the heart;
imaging a second plane of the heart by selective change of the direction of beam scanning with the plane orientation control while maintaining the probe in contact with the acoustic window;
storing information describing the orientations of the first and second planes in the storage device;
introducing a contrast agent into the myocardium of the heart;
acquiring a heart cycle waveform of the heart; and
initiating acquisition of images of the first and second planes of the heart by use of the stored information and in synchronism with the heart cycle waveform.

16. The method of claim 15, wherein initiating acquisition further comprises acquiring images of the first and second planes during a single waveform.

17. The method of claim 16, wherein acquiring further comprises acquiring another set of images of the first and second planes a predetermined number of heart cycles following the first acquiring of images.

18. The method of claim 16, wherein acquiring images of the first and second planes of the heart further comprises acquiring less than all of the scanlines of the first and second planes alternately until complete images of the first and second planes have been acquired.

19. The method of claim 15, wherein initiating acquisition further comprises acquiring an image from a different plane in successive heart cycles.

20. The method of claim 15 further comprising:
following the first initiating acquisition of images of the first and second planes of the heart, increasing the heart rate; and
following increasing the heart rate, acquiring for a second time images of the first and second planes of the heart by use of the stored information and in synchronism with the heart cycle waveform.

* * * * *